(12) United States Patent
Norman et al.

(10) Patent No.: US 9,994,954 B2
(45) Date of Patent: Jun. 12, 2018

(54) VOLATILE DIHYDROPYRAZINLY AND DIHYDROPYRAZINE METAL COMPLEXES

(71) Applicant: AIR PRODUCTS AND CHEMICALS, INC., Allentown, PA (US)

(72) Inventors: John Anthony Thomas Norman, Encinitas, CA (US); Sergei Vladimirovich Ivanov, Schnecksville, PA (US); Xinjian Lei, Vista, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 639 days.

(21) Appl. No.: 14/329,323

(22) Filed: Jul. 11, 2014

(65) Prior Publication Data
US 2015/0030782 A1 Jan. 29, 2015

Related U.S. Application Data

(60) Provisional application No. 61/858,799, filed on Jul. 26, 2013.

(51) Int. Cl.
| | |
|---|---|
| C23C 16/46 | (2006.01) |
| C23C 16/40 | (2006.01) |
| C07D 241/12 | (2006.01) |
| C23C 16/18 | (2006.01) |
| C23C 16/455 | (2006.01) |

(52) U.S. Cl.
CPC .......... *C23C 16/406* (2013.01); *C07D 241/12* (2013.01); *C23C 16/18* (2013.01); *C23C 16/40* (2013.01); *C23C 16/45553* (2013.01)

(58) Field of Classification Search
CPC .................................................. C23C 16/406
See application file for complete search history.

(56) References Cited

U.S. PATENT DOCUMENTS

| | | |
|---|---|---|
| 7,064,224 B1 | 6/2006 | Lei et al. |
| 8,084,145 B2 | 12/2011 | Inoue et al. |
| 2005/0221123 A1 | 10/2005 | Inoue et al. |
| 2006/0083857 A1 | 4/2006 | Meiere |
| 2007/0054487 A1 | 3/2007 | Ma et al. |
| 2009/0291208 A1 | 11/2009 | Gordon et al. |
| 2012/0231611 A1 | 9/2012 | Gatineau et al. |
| 2013/0023669 A1 | 1/2013 | Korolev et al. |
| 2013/0059077 A1 | 3/2013 | Thompson et al. |
| 2013/0089678 A1 | 4/2013 | Dussarrat et al. |
| 2013/0089680 A1 | 4/2013 | Dussarrat et al. |

FOREIGN PATENT DOCUMENTS

| | | |
|---|---|---|
| EP | 0952156 | 10/1999 |
| JP | 2005314414 | 11/2005 |
| JP | 2006511716 | 4/2006 |
| JP | 2006257073 | 9/2006 |
| JP | 2008516956 | 5/2008 |
| TW | 562800 | 11/2003 |
| WO | 2005030714 | 4/2005 |
| WO | 2012057883 | 5/2012 |
| WO | 2012057884 | 5/2012 |

OTHER PUBLICATIONS

J. Armand, et al, "Electrochemical and Chemical Reduction of Furopyraxines, Thienopyrazines, Furoquinoxalines, and Thienoquinoxalines", J. Org. Chem., 1991, 4840-4845.

C-M. Liu, et al, "A Novel Nickel(II) Complex Adopting a cis-Configuration: Solvothermal Synthesis and Crystal Structure of [NiL2(H2O)4] (L=1,4-Dihydropyrazine-2,3-dione-5,6-dicarboxylate)", Eur. J. Inorg. Chem., 2002, 1595-1598.

S. Kim, et al, "Local Epitaxial Growth of Ru Thin Films by Atomic Layer Deposition at Low Temperature", Journal of the Electrochemical Society, 2011, D477-D482.

Titta Aaltonen, et al, Ruthenium Thin Films Grown by Atomic Layer Deposition, Chemical Vapor Deposition, 2003, 45-49.

D. Gopal, et al, "A Novel Monoalkylation of Symmetrical a-Diones", Tetrahedron Letter, 39, 1988, 1877-1880.

Sang-Hyeok Choi, et al, "Thermal Atomic Layer Deposition (ALD) of Ru Films for Cu Direct Plating", Journal of the Eletrochemical Society, 2011, D351-D356.

J. Swerts, et al, "Scalability of plasma enhanced atomic layer deposited ruthenium films for interconnect applications", J. Vap. Sci. Technol., 2012, 01A103-1-01A103-6.

Keith Gregorczyk, et al, Atomic Layer Deposition of Ruthenium Using the Novel Precursor bis(2,6,6-trimethyl-cyclohexadienyl)ruthenium, Chemistry of Materials, 2011, 2650-2656.

K. Kukli, et al, "Atomic layer deposition of Ru films from bix(2,5-dimethylpyrrolyl)ruthenium and oxygen", Thin Solid Films, 2012, 2756-2763.

Ja-Yong Kim, et al, "Ru Films from Bis(ethylcyclopentadienyl)ruthenium Using Ozone as a Reactant by Atomic Layer Deposition for Capacitor Electrodes", Journal of Electrochemical Society, 2012, H560-H564.

S. Yim, et al, "Nucleation kinetics of Ru on silicon oxide and silicon nitride surfaces deposited by atomic layer deposition", Journal of Applied Physics, 2008, 113509-1-113509-9.

H. Li, "Vapor Deposition of Ruthenium from an Amidinate Precursor", Journal of the Electrochemical Society, 154, 2007, D642-D647.

*Primary Examiner* — Paul V Ward
(74) *Attorney, Agent, or Firm* — Rosaleen P. Morris-Oskanian; Lina Yang

(57) ABSTRACT

A composition comprising dihydropyrazinyl anions that can be coordinated as 6 electron ligands to a broad range of different metals to yield volatile metal complexes for ALD and CVD depositions are described herein. Also described herein are undeprotonated dihydropyrazines that can coordinate to metals as stabilizing neutral ligands. In one embodiment, the composition is used for the direct liquid injection delivery of the metal dihydropyrazinyl complex precursor to the chamber of an ALD or CVD chamber for the deposition of metal-containing thin films such as, for example, ruthenium or cobalt metal films.

2 Claims, 4 Drawing Sheets

VOLATILE DIHYDROPYRAZINLY AND DIHYDROPYRAZINE METAL COMPLEXES

CROSS-REFERENCE TO RELATED APPLICATIONS

This application claims benefit of U.S. Provisional Application No. 61/858,799, filed Jul. 26, 2013. The disclosure of this provisional application is hereby incorporated by reference in its entirety.

BACKGROUND OF THE INVENTION

Described herein are dihydropyrazine ligands that can be used, for example, to synthesize metal complexes such as, without limitation, ruthenium and cobalt complexes for use as ALD or CVD precursors. Also described herein are complexes comprising dihydropyrazine ligands and methods for making or using same.

The electronics industry continues to source volatile metal containing precursors for vapor deposition processes, including chemical vapor deposition (CVD) and atomic layer deposition (ALD), for fabricating conformal metal containing films on substrates, such as silicon, metal nitride, metal oxide and other metal-containing layers, using these metal-containing precursors. In these techniques, a vapor of a volatile metal complex is introduced into a process chamber where it contacts the surface of a silicon wafer whereupon a chemical reaction occurs that deposits a thin film of pure metal or a metal compound. CVD occurs if the precursor reacts at the wafer surface either thermally or with a reagent added simultaneously into the process chamber and the film growth occurs in a steady state deposition. CVD can be applied in a continuous or pulsed mode to achieve the desired film thickness. In ALD, the precursor is chemisorbed onto the wafer as a self-saturating monolayer, excess unreacted precursor is purged away with an inert gas such as argon, then excess reagent is added which reacts with the monolayer of chemisorbed precursor to form metal or a metal compound. Excess reagent is then purged away with inert gas. This cycle can then be repeated multiple times to build up the metal or metal compound to a desired thickness with atomic precision since the chemisorption of precursor and reagent are self-limiting. ALD provides the deposition of ultra-thin yet continuous metal containing films with precise control of film thickness, excellent uniformity of film thickness and outstandingly conformal film growth to evenly coat deeply etched and highly convoluted structures such as interconnect vias and trenches. Suitable metal precursors for ALD include those which are thermally stable to preclude any thermal decomposition occurring during the chemisorption stage yet are chemically reactive towards added reagent. Additionally, it is important that the metal precursors are monomeric for maximum volatility and clean evaporation leaving only a trace of involatile residue. It is also desirable that the precursors have high solubility in hydrocarbon solvents to form solutions which can be used for Direct Liquid Injection (DLI) to deliver precursor vapor to the CVD or ALD reactor. Hydrocarbon solvents such as cyclooctane and mesitylene are particularly attractive since they are relatively high boiling points liquids and can be readily dried to low moisture levels.

Ruthenium and cobalt are particularly attractive metals for CVD and ALD processes in the fabrication of semiconductor devices. The deposition of ultra-thin films of ruthenium can be used to create electrodes in DRAM capacitor cells or provide a copper adhesion promoting thin film grown onto copper diffusion barrier materials such as titanium nitride or tantalum nitride. Ultra-thin continuous ruthenium films can also be used as seed layers upon which copper metal can be directly electroplated. Similarly, thin cobalt layers can also be applied as adhesion promoting films for titanium nitride or tantalum nitride. Alternatively, cobalt can be deposited as a 'capping film' onto copper interconnect lines. When depositing either metal onto titanium nitride, tantalum nitride or other substrates which can be reactive towards the element oxygen, it is especially desirable that the ruthenium and cobalt complexes do not contain the element oxygen as this will tend to form metal oxides which can lead to electrical failures within the device being fabricated.

There are numerous ruthenium precursors reported in the chemical literature, but a common process challenge encountered when using them in ALD is their long incubation times towards forming a continuous metal film and the need to use oxygen or ozone as a reagent. Long incubation times are a result of low metal atom deposition (nucleation) densities in the first ALD cycles which slowly increase with further cycles since the nuclei tend to act as sites for further metal deposition. With a sufficient nucleation density established a linear relationship between ALD film thickness and number of ALD cycles is established. In this way, as many as 500 initial ALD cycles can be required to establish a steady growth rate of a ruthenium film (S. Yim et al, *Journal of Applied Physics,* 103, 113509, 2008). Nucleation densities can be enhanced by the application of plasma during the ALD process, but the strong directional vectoring of plasma tends to degrade the uniformity of deposition compared to thermal ALD, especially on the vertical side walls of deeply etched structures which can be 'shadowed' from the plasma. On the other hand, the use of oxygen and ozone reagents can be a problematic in their ability to oxidatively damage barrier films such as titanium nitride and tantalum nitride and also lead to roughening and etching of the ruthenium metal. In this regard, there is a strong need to develop ruthenium precursors which can deposit ruthenium metal by chemically reductive processes to therefore avoid oxidative damage. Suitable reagents for reduction include, but are not limited to: hydrogen, ammonia, amines, hydrazines, silanes, alanes and boranes. Most highly desired processes would include combinations of ruthenium precursors with reducing agents where neither contains the element oxygen. Similarly, there is a need for reductive growth of cobalt metal films from oxygen free cobalt precursors under reducing conditions. So, in summary there is a need for oxygen free ruthenium and cobalt precursors which can deposit metallic ruthenium and cobalt by reduction.

Other metal precursors described in the prior art include, without limitation, one or more of the following cyclopentadienyl (Cp), pyrrole, imidazole, diene, CO, alkyl substituted phenyl, amidinates, guanidinates or combinations thereof. However, the ligands and complexes described herein differ from those in the prior art because they are based on non-aromatic dihydropyrazine ligand(s) which allow for high reactivity for growing metal films by ALD and CVD and are oxygen free.

BRIEF SUMMARY OF THE INVENTION

Described herein are metal hydropyrazine containing complexes having Formula 3A through 3E described herein. In certain embodiments, the metal M is selected from Ru or Co. In certain embodiments, the complexes can be used, for example, for direct liquid injection (DLI) for ALD and CVD processes. These complexes can further comprise one or more solvents, such as a hydrocarbon or other solvent, and be packaged or housed in a stainless steel container.

Also described herein are N-alkyldihydropyrazines and N-trialkylsilydihydropyrazines.

Also described herein are ALD and CVD deposition processes that use the metal hydropyrazine containing complexes, more specifically ruthenium and cobalt containing complexes, with a reducing agent selected from hydrogen, ammonia, hydrazines, silanes, boranes in the deposition process.

Also described herein are ALD and CVD deposition processes that use the metal hydropyrazine containing complexes, more specifically ruthenium and cobalt containing complexes, with oxidizing agents such as ozone or oxygen.

Compositions comprising metal dihydopyrazinyl complexes are described herein which are useful for the DLI delivery of these precursors for vapor deposition processes such as atomic layer deposition (ALD) and chemical vapor deposition (CVD) growth of metal containing films. In order for these precursors to be delivered via DLI, these precursors should also be readily dissolved at a high enough concentration in order to form compositions suitable for DLI delivery. The compositions of metal dihydopyrazinyl complexes described herein exhibit both volatility and thermal stability under conditions of vaporization. In addition, they are highly effective as precursors for metal film growth and any other application which requires volatile sources of metal precursors.

In a still further aspect there is provided a method for forming a metal oxide film on a substrate wherein the film comprises a thickness, the method comprising:
  a. introducing a metal dihydopyrazinyl complex selected from a Formula 3A, 3B, 3C, 3D, 3E, 3F, 3G, and 3H complex or combinations thereof;
  b. chemisorbing the metal dihydopyrazinyl complex onto the substrate;
  c. purging away the metal dihydopyrazinyl complex using a purge gas;
  d. providing an oxygen source to the metal dihydopyrazinyl complex onto the heated substrate to react with the sorbed the metal dihydopyrazinyl complex; and
  e. optionally purging away any unreacted oxygen source wherein the steps a through d are repeated until the desired thickness of film is obtained.

DETAILED DESCRIPTION OF THE INVENTION

Figure 1:
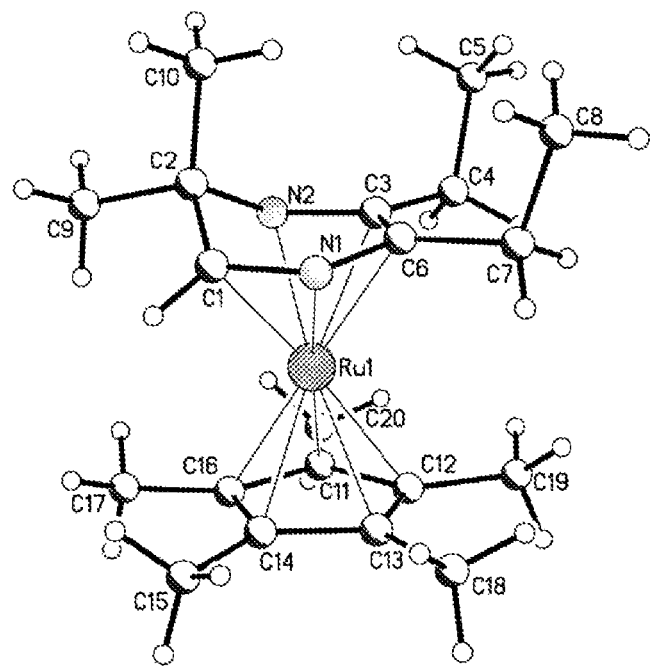
FIG. 1 is an illustration of the structure of ruthenium (pentamethylcyclopentadienyl)(2,2-dihydro-3,3-dimethyl-5,6-diethylpyrazinyl).

Described herein are compositions comprising dihydropyrazinyl anions that can be coordinated as 6 electron ligands to a broad range of different metals to yield volatile complexes for ALD and CVD. In certain embodiments, highly sterically substituted dihydroprazinyl anions are suitable for complexes comprising alkaline earths metals. In other embodiments, less sterically substituted dihydopyrazinyls are suitable for complexes further comprising transition metal and lanthanide metals. In still further embodiments, neutral undeprotonated dihydropyrazines can be used, for example, as 4 electron donor ligands. With regard to the later embodiment, a zero valent ruthenium complex can be made from dihydropyrazine (4 electron), ruthenium (0) (8 electrons) and toluene (6 electrons) for an 18 electron complex. An advantage of the dihydropyrazine ligand described herein is that it can be reactive with water or hydroxyl (OH) groups due to hydrogen bonding to the ring nitrogens which leads to hydrolysis/breaking the ring open subsequent metal or metal oxide film deposition. Not being bound to theory, the reactivity should be greater in this regard compared to similar complexes having cyclohexadiene ligands which are not hydrolytically labile. In yet a further embodiment, neutral and deprotonated dihydropyrazines can be used in conjuction with other ligands such as cyclopentadiene (Cp), pyrrole, imidazole, amidinate, guanidinate, diimines, ketoimines, diketones or the like to form mixed ligand complexes. The resulting compositions or complexes comprising the dihydroprazine ligand disclosed herein allow them to be both volatile for deposition processes, more specifically atomic layer deposition processes, yet thermally stable under conditions of vaporization. In addition to the foregoing, the compounds or complexes and compositions comprising same are useful as precursors for metal film growth, such as without limitation ruthenium or cobalt metal films, and any other application which requires volatile sources of metal precursors.

The metal dihydropyrazinyl complexes described herein contain one or more metals selected from a Group 2 to Group 16 or a Group 4 to Group 16. In certain embodiments of the Formulae described herein, M is a metal selected from Group 4 to 16, including without limitation, Fe, Co, Ni, Cr, Mn, Ru, Rh, Pd, Os, Ir, Pt, Cu, Zn, In, Ge, Sn, Sb, Te, Bi, Ti, Zr, Hf, V, Nb, Ta, Cr, Mo, W, Al, In, Sn, Sb, Bi; La, Ce, Pr, Nd, Pm, Sm, Eu, Gd, Tb, Dy, Ho, Er, Tm, Yb and combinations thereof. In one particular embodiment, M is Ru. In another particular embodiment, M is Co.

Described herein is the synthesis of metal dihydropyrazinyl complexes, such as without limitation, oxygen free ruthenium and cobalt precursors based upon dihydropyrazine ligands. These new compounds are monomeric, cleanly volatile and highly soluble in hydrocarbon solvents. The dihydropyrazine ligands can be incorporated into these new complexes in their deprotonated form as dihydropyrazinyl anions, as dihydropyrazinyl radical anions, or as neutral (un-deprotonated) ligands. These different ligand configurations are shown in Formula 1.

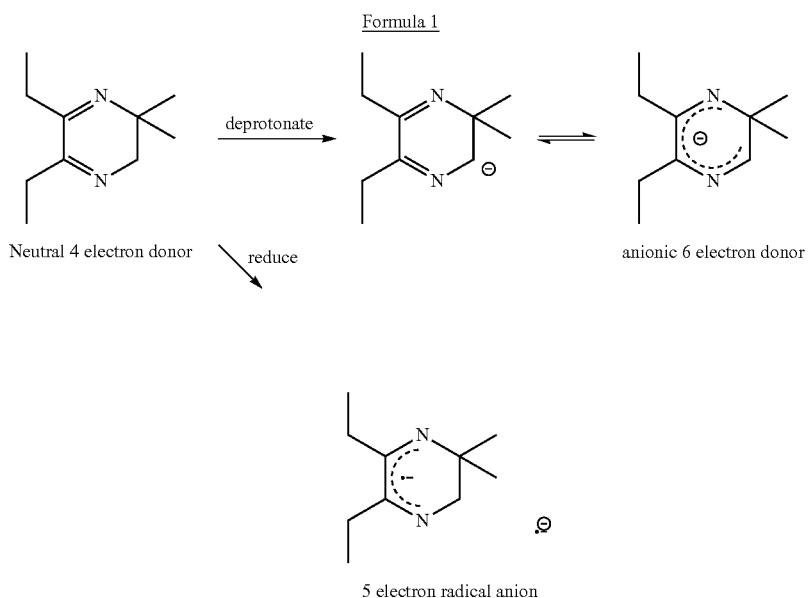

Formula 1

Additionally, N-alkyldihydropyrazines or N-trialkylsilyl-dihydropyrazines can also be incorporated into these new complexes as neutral molecules or as N-alkyldihydropyrazinyl or N-trialkylsilyldihydropyrazinyl radical anions. These ligand configurations are shown in Formula 2 for N-trialkylsilyldihydropyrazine.

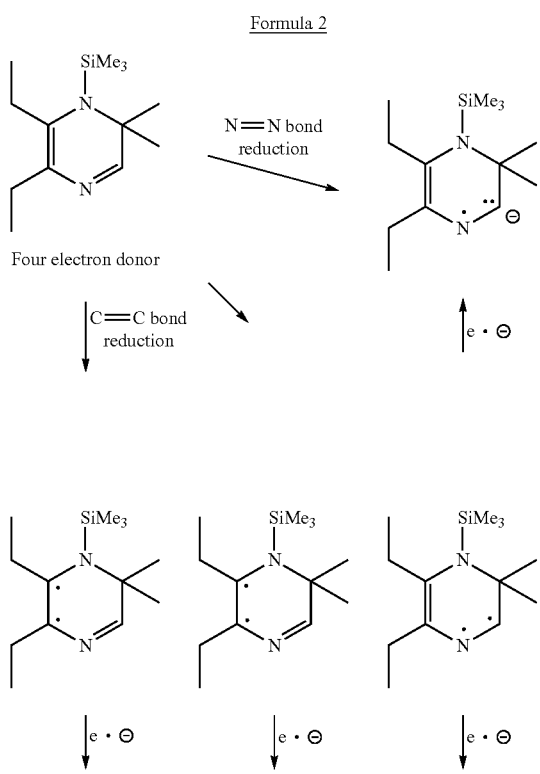

Formula 2

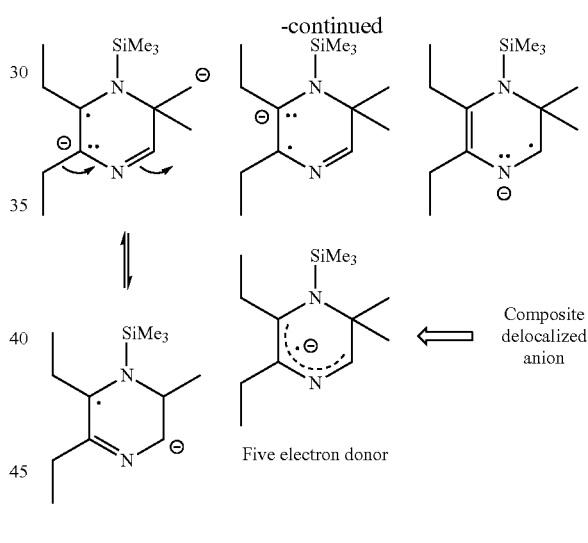

Metal dihydopyrazinyl complexes can be formed that contain more than one dihydropyrazinyl anion, or more than one dihydropyrazinyl radical anion, or more than one N-alkyldihydropyrazinyl radical anion or more than one N-trialkylsilyldihydropyrazinyl radical anion.

In another embodiment, complexes can be formed which contain only one dihydropyrazinyl anion, or only one dihydropyrazinyl radical anion or only one N-alkyldihydropyrazinyl radical anion or only one trialkylsilyldihydropyrazinyl radical anion in combination with other different anions such as pentamethylcyclopentadienyl. These complexes are shown in Formulae 3A, 3B and 3C wherein $R^1$, $R^2$, $R^3$, $R^4$ are each independently selected from a $C_1$-$C_6$ linear, branched or cyclic alkyl group; $R^5$ is independently selected from a H atom or a linear, branched, or cyclic $C_1$-$C_6$ alkyl group; $R^6$ is independently selected from a $C_1$-$C_3$ linear or branched alkyl group; (L) is an anion selected from cyclopentadienyl, pentamethylpentadienyl, dimethylpentadienyl, trimethylpentadienyl, methylcyclopentadienyl, ethylcyclopentdienyl, imidazolyl, trialkylimidazolyl, pyrrolyl, alkyl pyrrolyl; M is a divalent metal; x=1 or 2; x+y=2; and X in Formula 3C is independently selected from a H atom, a $C_1$-$C_6$ linear, branched, or cyclic alkyl group, and $SiR^6$ where $R^6$ is independently selected from a $C_1$-$C_3$ linear or branched alkyl group.

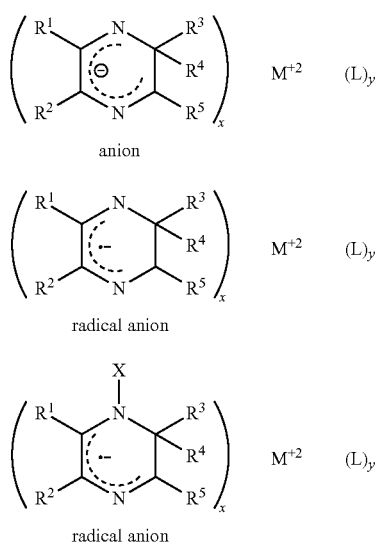

Formula 3A

Formula 3B

Formula 3C

In a still further embodiment, the above formulae 3A, 3B, and 3C can comprise M that can have a "+1" oxidation state or a monovalent metal. In these embodiments, $R^1$, $R^2$, $R^3$, $R^4$, $R^5$, $R^6$, and (Q) is a neutral ligand, such as without limitation, benzene or an alkylated benzene are as described herein however when x is 1; y becomes 0 (e.g., L is not present); and new variable 'z' is 1. A general example of formulae 3A, 3B, and 3C wherein M is a monovalent would be the following: $(anion)_x M^{+n}(L)_y(Q)_z$. More specific examples of these compounds are represented by the following Formulae 3F, 3G, and 3H.

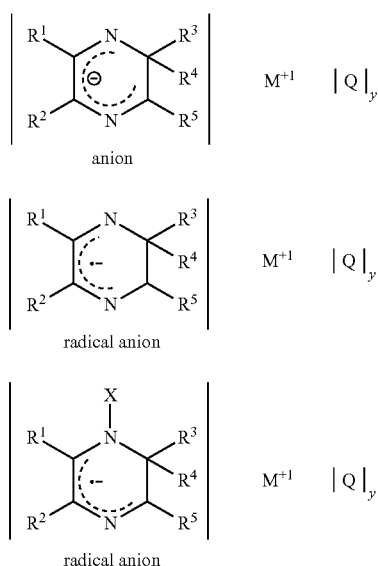

Formula 3F

Formula 3G

Formula 3H

Complexes can also be formed containing neutral (undeprotonated) dihydropyrazines as shown in Formula 3D where $R^1$, $R^2$, $R^3$, $R^4$ are each independently selected from a $C_1$-$C_6$ linear, a branched, or a cyclic alkyl group; $R^5$ is independently selected from a H atom or a $C_1$-$C_6$ linear, branched, or cyclic alkyl group; (L) is an anion selected from cyclopentadienyl, pentaalkylcyclopentadienyl, pentamethylpentadienyl, dimethylpentadienyl, trimethylpentadienyl, methylcyclopentadienyl, ethylcyclopentdienyl, imidazolyl, trialkylimidazolyl, pyrrolyl, and alkyl pyrrolyl; M is a monovalent metal; x=1 or 2; y=1, and Z is independently selected from a H atom, a $C_1$-$C_6$ linear, branched, or cyclic alkyl group, and $SiR^6$ where $R^6$ is independently selected from a linear, branched, or cyclic $C_1$-$C_3$ alkyl group.

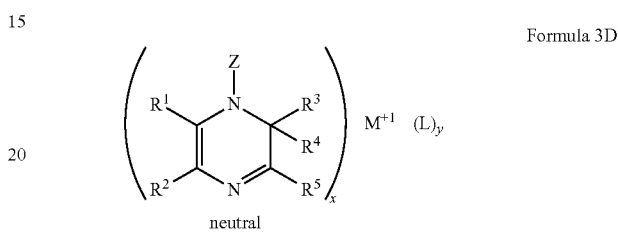

Formula 3D

Complexes can also be formed containing neutral (undeprotonated) dihydropyrazines as shown in Formula 3E wherein $R^1$, $R^2$, $R^3$, $R^4$ are each independently a $C_1$-$C_6$ linear, branched or cyclic alkyl group; $R^5$ is a H atom or a $C_1$-$C_6$ linear, branched, or cyclic alkyl group; (Q) is benzene or an alkylated benzene; M is a metal in 0 oxidation state, x=1 or 2; y=1, Z is independently selected from a H atom or a $C_1$-$C_6$ linear, branched, or cyclic alkyl group or $SiR^6$ where $R^6$ is a linear, branched, or cyclic $C_1$-$C_3$ alkyl group.

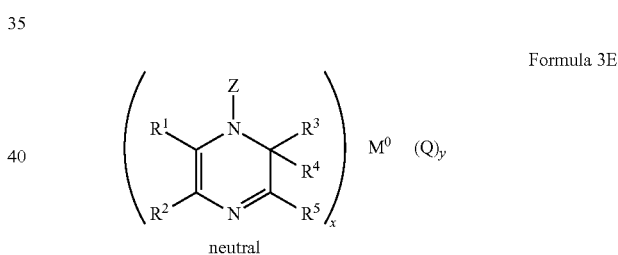

Formula 3E

Figure 3:
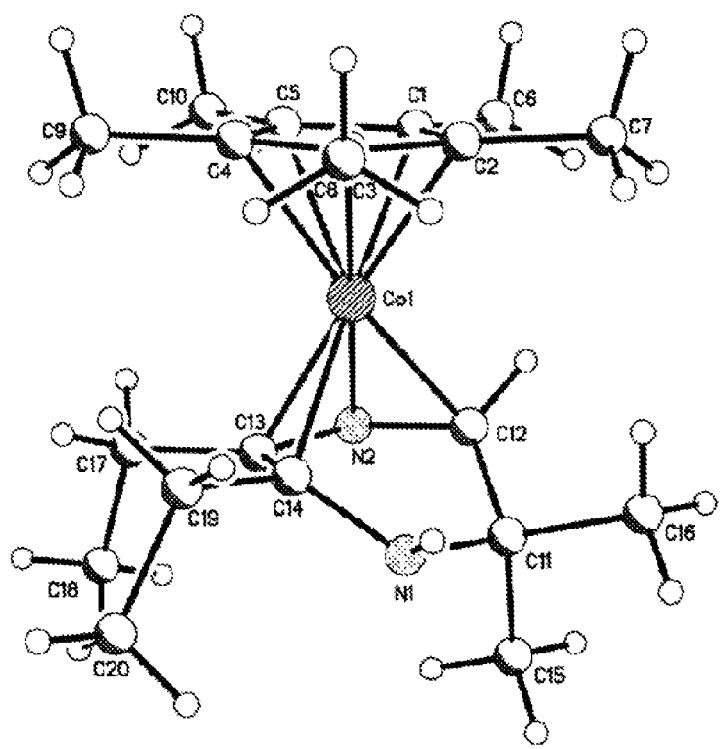
FIG. 3 is an illustration of the structure of cobalt (pentamethylcyclopentadienyl)(2,2-dihydro-3,3-dimethyl-5,6-diethylpyrazine).

In formulae 3A, 3B, 3C and 3D above, (L) can also be a dihydropyrazine anion, dihydropyrazine radical anion, N-alkyldihydropyrazine radical anion, N-trialkylsilyldihydropyrazine radical anion that is different from the (dihydropyrazine)x The dihydropyrazinyl anions of this disclosure are shown to coordinate to ruthenium in an eta-5 mode, as illustrated in FIG. 1) for ruthenium (pentamethylcyclopentadienyl)(2,2-dihydro-3,3-dimethyl-5,6-diethyl pyrazinyl) where Ru1 bonds to C1, N1, C6, C3 and N2 of the DMDEP ligand. In this way, the DMDEP anion acts as a 6 electron donor where formally 2 electrons are provided by the anion negative charge then an additional 2 electrons from each of the ligand's two double bonds. In this way, the dihydropyrazinyl anions can aid in providing an 18 electron coordination sphere around a transition metal to provide a stable complex. Thus, in the example of ruthenium (pentamethylcyclopentadienyl)(2,2-dihydro-3,3-dimethyl-5,6-diethyl pyrazinyl), six (d) electrons are provided by $Ru^{+2}$, six from the dihydropyrazinyl anion and six electrons from the pentamethylcyclopentadienyl anion to give a total of 18 electrons. Neutral (undeprotonated) dihydropyrazine ligands, N-alkyldihydropyrazines or trialkylsilyldihydropyrazines can coordinate to metals in a similar sideways eta-4 mode as a four electron donors, two electrons being provided from each of the ligands two double bonds. Referring now to FIG. 3 or the structure of cobalt(pentamethylcyclopentadienyl)(2,2-dihydro-3,3-dimethyl-5,6-diethylpyrazine), eight (d) electrons are provided by $Co^{+1}$, six electrons are provided from the pentamethylcyclopentadienyl anion and four electrons from the dihydropyrazine ligand to give a total of 18 electrons. N-alkyldihydropyrazines and N-trisilyalkyldihydropyrazines can be reduced by one electron to form N-alkyldihydropyrazinyl and N-trisilyalkyldihydropyrazinyl radical anions respectively which have their negative charge delocalized across four atoms of the dihydropyrazine ring and can donate 2 electrons from the formal negative charge, two electrons from the double bond and one electron from the reducing added electron to give a total of 5 electrons. These radical anion configurations are also shown above in Formula 2 for N-trisilylalkyldihydropyrazines.

While not wishing to be bound by theory, since the dihydropyrazine ligands and their anions are non-aromatic, their reduction by hydrogen to their corresponding amines is not hindered by loss of aromatic stabilization and the reduction is catalyzed by the being coordinated to ruthenium or other metals. Once the dihydropyrazine ligand is reduced it can no longer provide stabilization to the metal which can then in turn be reduced to its metallic state.

Figure 5:
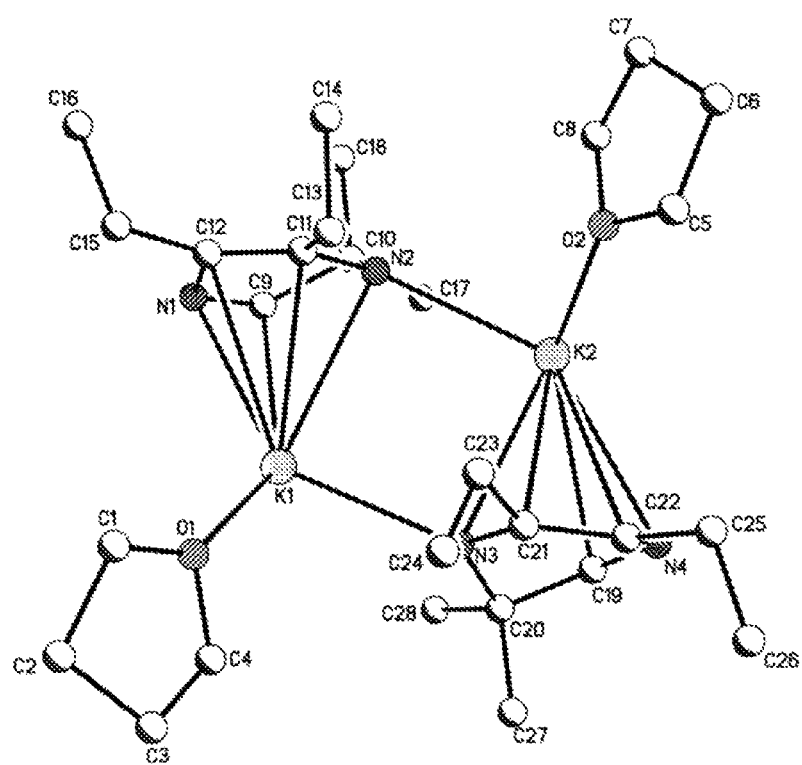
FIG. 5 is an illustration of the structure of potassium (2,2-dihydro-3,3-dimethyl-5,6-diethylpyrazinyl)(tetrahydrofuran).

A remarkable aspect of the complexes of this disclosure is that according to the chemical literature (D. Gopal et. al Tetrahedron Letters, 39, 1877-1880, 1998) ("Gopal et. al."), dihydropyrazines of the type described herein, or alkyl substituted with dialkyl substituted quaternary carbon at position 3, undergo exocyclic deprotonation to yield thermally unstable anions whose negative charge is not delocalized around the dihydropyrazinyl ring, as illustrated below in Formula 4. By contrast, Applicants have shown herein that endocyclic ligand deprotonation of alkyl substituted dihydropyrazines can readily be achieved to yield anions whose charge is delocalized across five atoms of the dihydropyrazinyl ring, as illustrated in Formula 5, and further that the resulting anions are thermally stable. The Gopal et al. reference also reports dimerization of the dihydropyrazine to occur upon storage at −15° C. However, Applicants have found that 2,2-dihydro-3,3-dimethyl-5,6-diethylpyrazine is stable at room temperature. Further, ruthenium and cobalt complexes based upon the dihydropyrazines described herein are also stable. Applicants have also found that potassium (2,2-dihydro-3,3-dimethyl-5,6-diethyl pyrazinyl) (tetrahydrofuran) is thermally stable by isolating it at room temperature as a crystalline solid and proving it to be eta-5 coordinated to potassium (+1) by X-ray crystallography, as shown in FIG. 5. In summary, the thermal stability of the dihydropyrazines described herein and its endocyclic deprotonation provide stable and fully delocalized anions from which stable and volatile metal complexes can be prepared. Also, described herein are N-alkyldihydropyrazines and N-trialkylsilydihydropyrazines which believe will also provide stable yet volatile metal complexes.

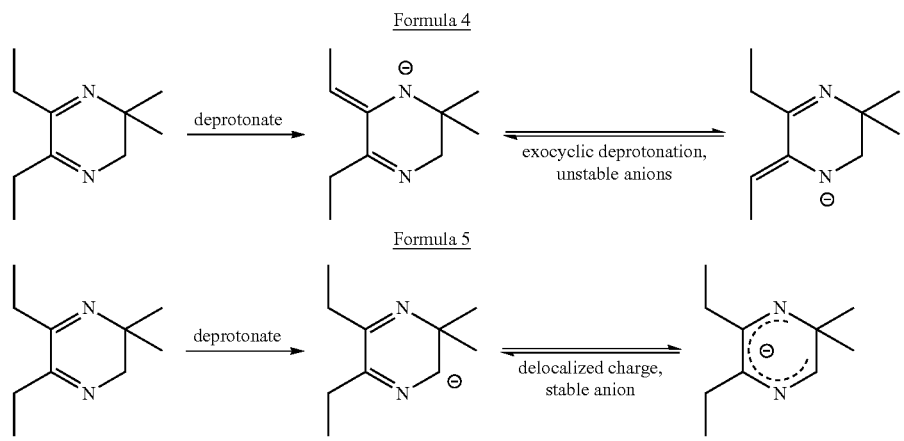

Formula 4

Formula 5

The metal dihydopyrazinyl complexes or compositions described herein are highly suitable for use as volatile precursors for ALD, CVD, pulsed CVD, plasma enhanced ALD (PEALD) or plasma enhanced CVD (PECVD) for the manufacture of semiconductor type microelectronic devices, such as microcapacitor cells for memory applications such as DRAM devices. The complexes are also highly useful for the manufacture of pyrodetector devices. The method used to form the metal-containing films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the metal-containing film is deposited using an ALD process. In another embodiment, the metal-containing film is deposited using a CCVD process. In a further embodiment, the metal-containing film is deposited using a thermal CVD process. The term "reactor" as used herein, includes without limitation, reaction chamber or deposition chamber.

In certain embodiments, the method disclosed herein avoids pre-reaction of the metal precursors by using ALD or CCVD methods that separate the precursors prior to and/or during the introduction to the reactor. In this connection, deposition techniques such as ALD or CCVD processes are used to deposit the dielectric film. In one embodiment, the film is deposited via an ALD process by exposing the substrate surface alternatively to the one or more metal dihydopyrazinyl complex composition, oxygen source, reducing agent, and/or other precursor or reagent. Film growth proceeds by self-limiting control of surface reaction, the pulse length of each precursor or reagent, and the deposition temperature. However, once the surface of the substrate is saturated, the film growth ceases.

Depending upon the deposition method, in certain embodiments, the one or more, metal dihydopyrazinyl complexes may be introduced into the reactor at a predetermined molar volume, or from about 0.1 to about 1000 micromoles. In this or other embodiments, the metal dihydopyrazinyl complex precursor may be introduced into the reactor for a predetermined time period. In certain embodiments, the time period ranges from about 0.001 to about 500 seconds.

In certain embodiments, the films deposited using the methods described herein are formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 standard cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is greater than 0.01 seconds, while the water pulse duration can have a pulse duration that is greater than 0.01 seconds. In yet another embodiment, the purge duration between the pulses that can be as low as 0 seconds or is continuously pulsed without a purge in-between.

In certain embodiments, the process employs a reducing agent. The reducing agent is typically introduced in gaseous form. Examples of suitable reducing agents include, but are not limited to, hydrogen gas, hydrogen plasma, remote hydrogen plasma, silanes (i.e., diethylsilane, ethylsilane, dimethylsilane, phenylsilane, silane, disilane, aminosilanes, chlorosilanes), boranes (i.e., borane, diborane), alanes, germanes, hydrazines, ammonia, or mixtures thereof.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, and/or other precursors, source gases, and/or reagents may be performed by changing the time for supplying them to change the stoichiometric composition of the resulting film.

Energy is applied to the at least one of the precursor, oxygen-containing source, reducing agent, other precursors or combination thereof to induce reaction and to form the metal-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The metal dihydopyrazinyl complex precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. The precursor compositions described in this application can be effectively used as source reagents in DLI mode to provide a vapor stream of these metal dihydopyrazinyl complex precursors into an ALD or CVD reactor.

In certain embodiments, these compositions include those utilizing hydrocarbon solvents which are particularly desirable due to their ability to be dried to sub-ppm levels of water. Exemplary hydrocarbon solvents that can be used in the present invention include, but are not limited to, toluene, mesitylene, cumene (isopropylbenzene), p-cymene (4-isopropyl toluene), 1,3-diisopropylbenzene, octane, dodecane, 1,2,4-trimethylcyclohexane, n-butylcyclohexane, and decahydronaphthalene (decalin). The precursor compositions of this application can also be stored and used in stainless steel containers. In certain embodiments, the hydrocarbon solvent in the composition is a high boiling point solvent or has a boiling point of 100° C. or greater. The group metal dihydopyrazinyl complex precursor compositions of this application can also be mixed with other suitable metal precursors, and the mixture used to deliver both metals simultaneously for the growth of a binary metal oxide or nitride films.

In certain embodiments, the purity level of the precursor compositions is sufficiently high enough to be acceptable for reliable semiconductor manufacturing. In certain embodiments, the metal-containing precursors and compositions comprising same described herein comprise less than 2% by weight, or less than 1% by weight, or less than 0.5% by weight of one or more of the following impurities: free amines, free halides or an halogen ion, and higher molecular weight species. Higher purity levels of the metal dihydopyrazinyl complex precursors described herein can be obtained through one or more of the following processes: purification, adsorption, and/or distillation.

In certain embodiments, the gas lines connecting from the precursor canisters to the reaction chamber are heated to one or more temperatures depending upon the process requirements and the container comprising the composition is kept at one or more temperatures for bubbling. In other embodiments, a composition comprising the metal dihydopyrazinyl complex precursor is injected into a vaporizer kept at one or more temperatures for direct liquid injection.

A flow of argon and/or other gas may be employed as a carrier gas to help deliver the vapor of the at least one group metal dihydopyrazinyl complex precursor to the reaction chamber during the precursor pulsing. In certain embodiments, the reaction chamber process pressure is about 1 Torr.

In a typical ALD or CCVD process, the substrate such as a silicon oxide substrate is heated on a heater stage in a reaction chamber that is exposed to the metal dihydopyrazinyl complex precursor initially to allow the complex to chemically adsorb onto the surface of the substrate.

A purge gas such as argon purges away unabsorbed excess complex from the process chamber. After sufficient purging, a nitrogen-containing source may be introduced into reaction chamber to react with the absorbed surface followed by another gas purge to remove reaction by-products from the chamber. The process cycle can be repeated to achieve the desired film thickness.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting dielectric film.

In another embodiment of the method disclosed herein, the metal or metal oxide films is formed using an ALD deposition method that comprises the steps of:

providing a substrate in a reactor;
introducing into the reactor a containing composition comprising a metal dihydopyrazinyl complex containing precursor selected from a Formula 3A, 3B, 3C, 3D, 3E compound or combinations thereof;
chemisorbing the metal dihydopyrazinyl complex containing precursor onto a substrate;
purging away the unreacted metal dihydopyrazinyl complex metal containing precursor using a purge gas;
providing an oxygen source to the metal dihydopyrazinyl complex metal containing precursor onto the heated substrate to react with the sorbed at least one metal dihydopyrazinyl complex containing precursor; and
optionally purging away any unreacted oxygen source.

In yet another embodiment of the method disclosed herein, a metal film is formed using an ALD deposition method on a substrate wherein the film comprises a thickness, the method comprising:

a. introducing a metal dihydopyrazinyl complex comprising at least one selected from a Formula 3A, 3B, 3C, 3D, 3E compound or combinations thereof;

b. chemisorbing the metal dihydopyrazinyl complex onto the substrate;
c. purging away the a metal dihydopyrazinyl complex using a purge gas;
d. optionally providing a reducing agent to the metal dihydopyrazinyl complex onto the heated substrate to react with the sorbed metal dihydopyrazinyl complex; and
e. optionally purging away any unreacted reducing agent, and wherein the reducing agent can be selected from hydrogen, hydrogen plasma, ammonia, ammonia plasma, hydrogen/nitrogen plasma, alkylsilane and mixture thereof and wherein the steps a through e are repeated until the desired thickness of the metal film is obtained.

The above steps define one cycle for the method described herein; and the cycle can be repeated until the desired thickness of a film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component films, other precursors such as silicon-containing precursors, nitrogen-containing precursors, reducing agents, or other reagents can be alternately introduced into the reactor chamber.

In a further embodiment of the method described herein, the dielectric film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing a composition comprising the metal dihydopyrazinyl complex comprising at least one selected from a Formula 3A, 3B, 3C, 3D, 3E compound or combinations thereof; and providing an oxygen source into the reactor to at least partially react with the metal dihydopyrazinyl complex and deposit a metal film onto the one or more substrates. In certain embodiments of the CVD method, the reactor is maintained at a pressure ranging from 100 mTorr to 600 mTorr during the introducing step.

The above steps define one cycle for the method described herein; and the cycle can be repeated until the desired thickness of a film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting film.

For multi-component films, other precursors such as silicon-containing precursors, nitrogen-containing precursors, oxygen sources, reducing agents, and/or other reagents can be alternately introduced into the reactor chamber.

Described herein is a method of depositing a metal containing film by ALD or CVD comprising the use of compositions comprising metal dihydopyrazinyl complex precursors of the present invention described above. In one particular embodiment, there is provided a method of depositing a metal containing film by delivering a composition comprising the metal dihydopyrazinyl complex precursor and a compatible solvent to the reaction chamber by DLI delivery then reacting it with an oxygen source selected from the group consisting of water, alcohol, oxygen, ozone, nitrous oxide, nitrogen dioxide, hydrogen peroxide or combinations thereof to grow a metal containing film, using a reactor pressure between 0.001-1000 Torr and a temperature from ranging from 0-1000° C. Depending upon the identity of the metal, this method results in a deposition of a metal oxide of about 1 Angstrom (Å) or greater per cycle.

The present invention is also a method to grow dielectric films or metal films using one or more of the metal dihydopyrazinyl complex precursors described herein to form micro-electronic devices selected from the group consisting of dynamic random access memory (DRAM) memory cells and pyrometric devices.

Alternately, the present invention is a method of manufacturing microelectronic devices selected from the group consisting of: non-volatile ferroelectric microelectronic memory devices, display phosphors for electroluminescent displays, high Tc superconducting devices using the imidazolate structures of the present invention.

In yet another embodiment, the present invention is a method of growing a metal oxide or nitride film by ALD or CVD comprising; providing a metal dihydopyrazinyl complex dissolved in a solvent selected from the group consisting of: an ether, aminoether, amide, ester, aromatic or hydrocarbon solvent and delivering the resulting composition by a DLI system to provide a vapor stream of the resulting composition to grow the metal oxide or nitride film by ALD or CVD.

EXAMPLES

Example 1: Synthesis of 2,2-dihydro-3,3-dimethyl-5,6-diethylpyrazine (e.g., HDMDEP)

50.0 g (0.438 moles) 3,4-hexanedione were dissolved into 250 milliliters (ml) of tetrahydrofuran (THF) and 38.6 g (0.438 moles) of $H_2NC(Me)_2CH_2NH_2$ were added with stirring over 30 minutes maintaining 20-25° C. by ice bath cooling. The mixture was then stirred overnight. The mixture was then stirred with 20 grams(g) of anhydrous magnesium sulfate overnight, filtered and the THF removed by vacuum to yield a golden yellow liquid (58 g). This was then stood over 20 g of dried mole sieves for 2 days. The mole sieves were then removed and the crude material bulb to bulb transferred at 65 C/100 mTorr, collecting the final product as a very light yellow green liquid. The product yield was 47 g (65%). Gas chromatography-mass spectrometry (GCMS) showed the parent ion at 166 mu.

Example 2: Synthesis of ruthenium(pentamethylcyclopentadienyl)(2,2-dihydro-3,3-dimethyl-5,6-diethyl pyrazinyl) (e.g., RuCp*DMDEP)

Figure 2:
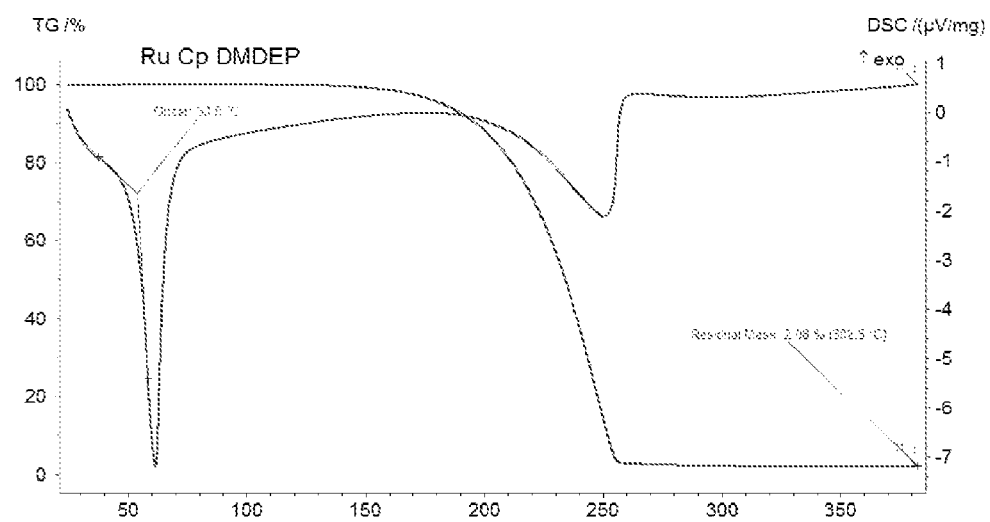
FIG. 2 provides the thermogravimetric analysis (TGA)/differential scanning calorimetry (DSC) result of ruthenium (pentamethylcyclopentadienyl)(2,2-dihydro-3,3-dimethyl-5,6-diethylpyrazinyl) (Ru(Cp)DMDEP).

Under a vented atmosphere of argon, 9.3 g (0.056 moles) of HDMDEP dissolved in 20 ml of tetrahydrofuran were added dropwise over 10 minutes to 10.66 g (0.053 moles) of potassium hexamethyldisilazane dissolved in 200 ml of tetrahydrofuran cooled to −78 C. The resulting mixture was stirred at −78° C. for 30 minutes then allowed to slowly warm to room temperature over two hours. The resulting solution of KDMDEP was then added via canula over 20 minutes to 14.25 g of chloro(pentamethylcyclopentadienyl) ruthenium (+2) tetramer (e.g., RuCp*Cl) (0.052 moles of ruthenium) stirring in 300 ml of tetrahydrofuran at room temperature. The mixture was then refluxed for 2 days. The solvent was then removed by vacuum and 300 ml of hexane added under argon. The resulting mixture was agitated for 20 minutes then filtered to give a dark brown filtrate. The hexane was removed by vacuum to yield a dark brown tar. The tar was then bulb-to-bulb distilled at 140° C./100 mTorr pressure to yield a golden yellow liquid which solidified over a two day period to give a crystalline mass. The supernatant liquid was transferred to a freezer at −20° C. for 3 day yielding a second crop of crystals. The two batches of crystals were then combined and vacuum distilled again at 140° C., discarding the first fraction which was trace excess dihydropyrazine, the collecting the main fraction as a golden brown oil which solidified into golden brown crystals over a two day period. Yield=11.0 g (52%). Melting point of 54° C., 2.08 wt % residue by TGA, as shown in FIG. 2. X-ray crystallography confirmed the structure as monomeric RuCp*(DMDEP).

$^1$H NMR: (500 MHz, D8 toluene): δ=0.42 (s, 3H), δ=1.14 (t, 3H), δ=1.44 (s, 3H), δ=1.45 (t, 3H), δ=1.67 (s, 15H), δ=2.4-2.5, 2.7-2.8 (m, 4H), δ=3.67 (s, 1H). GCMS showed the parent ion at 401 mu.

Example 3: Synthesis cobalt(pentamethylcyclopentadienyl)(2,2-dihydro-3,3-dimethyl-5,6-diethylpyrazine) (e.g., CoCp*HDMDEP)

Figure 4:
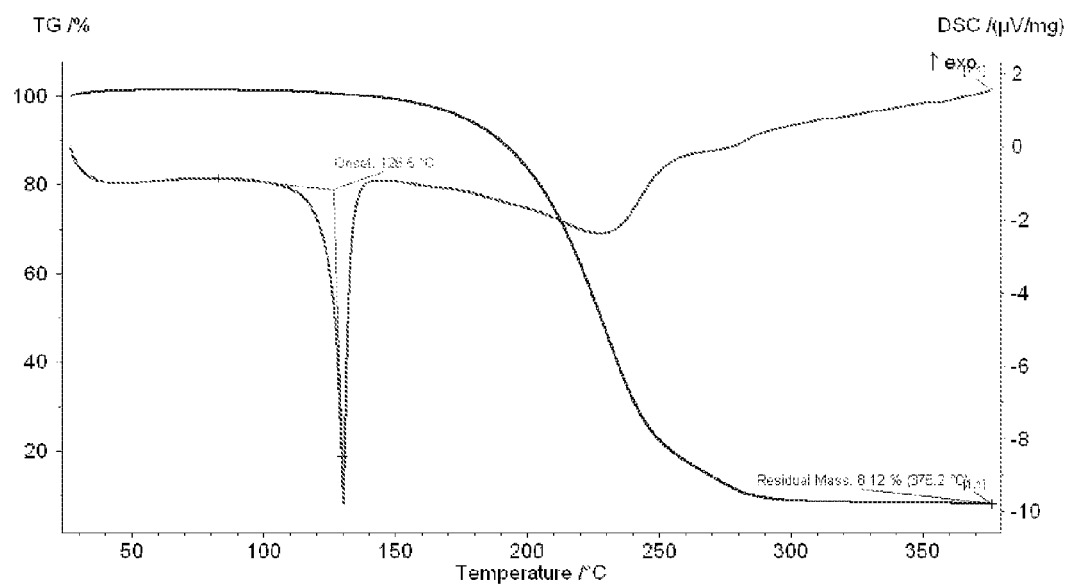
FIG. 4 provides the TGA/DSC result of cobalt (pentamethylcyclopentadienyl)(2,2-dihydro-3,3-dimethyl-5,6-diethylpyrazine).

Under an atmosphere of nitrogen, 0.68 g (0.005 moles) of pentamethylcyclopentadiene were added to 0.2 g (0.005 moles) of potassium hydride in 20 ml THF and the mixture warmed to 45 C under nitrogen for 2 hrs to yield a buff colored suspension. 0.65 g (0.005 moles) of cobalt dichloride were then added and the mixture stirred overnight at room temperature to yield a dark brown mixture. 1.02 g (0.005 moles) of KDMDEP (THF) solid dissolved in 5 ml THF was added and the mixture stirred overnight. THF was then removed by vacuum and the dark oily mass extracted with 30 ml hexane and filtered. The Hexane was removed by vacuum and the dark brown oil bulb to bulb distilled at 120 C/100 mTorr to give at first a red brown oil followed by a very dark red crystalline product. Yield=0.4 g (22%), MPt 126.5 C, TGA residue 8.12 wt % as shown in FIG. 4. GCMS showed the parent ion at 360 mu. $^1$H NMR: (500 MHz, D8 toluene): δ=0.95 (s, 3H), δ=0.97 (s, 3H), δ=1.01 (t, 3H), δ=1.42 (t, 3H), δ=1.45 (m, 1H), δ=1.71 (s, 15H), δ=1.73 (m, 1H), δ=2.20 (m, 1H), δ=2.4 (m, 1H), δ=3.29 (s, 1H).

X-ray crystallography confirmed the structure as monomeric CoCp*(HDMDEP) where Co1 bonds to C12, N2, C13, and C14 of HDMDEP ie eta-4 coordination.

Example 4: Synthesis of potassium(2,2-dihydro-3,3-dimethyl-5,6-diethylpyrazinyl)(tetrahydrofuran) (e.g., KDMDEP in THF)

Under an atmosphere of argon, 1.7 g (0.01 moles) HDMDEP in 5 ml THF were added to, 1.8 g (0.0090 moles) KHMDZ in 30 ml THF on dry ice over 2 minutes and stirred 90 mins on dry ice then warm to RT for 90 mins. The solvent, hexamethyldisilazane and undeprotonated HDMDEP were removed under vacuum to yield a crude solid. A small sample was then suspended in boiling hexane and THF added dropwise until the suspension dissolved. Upon cooling to room temperature small crystals formed which were shown by X-ray crystallography (FIG. 5) to be the desired 2,2-dihydro-3,3-dimethyl-5,6-diethylpyrazyl anion coordinating eta-5 to potassium where K1 bonds to C9, N1, C12, C11 and N2. One molecule of THF is also coordinated to each potassium ion. For the NMR sample all THF was pumped off and the sample prepared in deuterotetrahydrofuran. $^1$H NMR: (500 MHz, D8 THF): δ=0.78 (s, 6H), δ=0.94 (t, 3H), δ=1.04 (t, 3H), δ=2.03 (q, 2H), δ=2.31 (q, 2H), δ=4.85 (s, 1H).

Example 5: Synthesis of ruthenium (2,2-dihydro-3, 3-dimethyl-5,6-diethylpyrazine)(benzene)

1.33 g (0.006 moles)HDMDEP in 5 ml THF was added to 1.6 g (0.0054 moles) of potassium hexamethyldisilazane in 50 ml THF at −78 C then allowed to warm to room temperature over 2 hours (hrs). This solution was then added to 1.0 g (0.004 moles Ru) of RuCl$_2$.benzene in 50 ml of THF. The mixture was refluxed for 8 hrs then the solvent removed under vacuum and the resulting mass extracted with 100 ml of hexane and filtered. Hexane was removed under vacuum and the resulting brown oil was bulb-to bulb distilled at 150 C/100 mTorr give a golden brown oil distillate. GCMS showed Ru(HDMEP)(benzene) parent ion at 346 mu.

Figure 6:
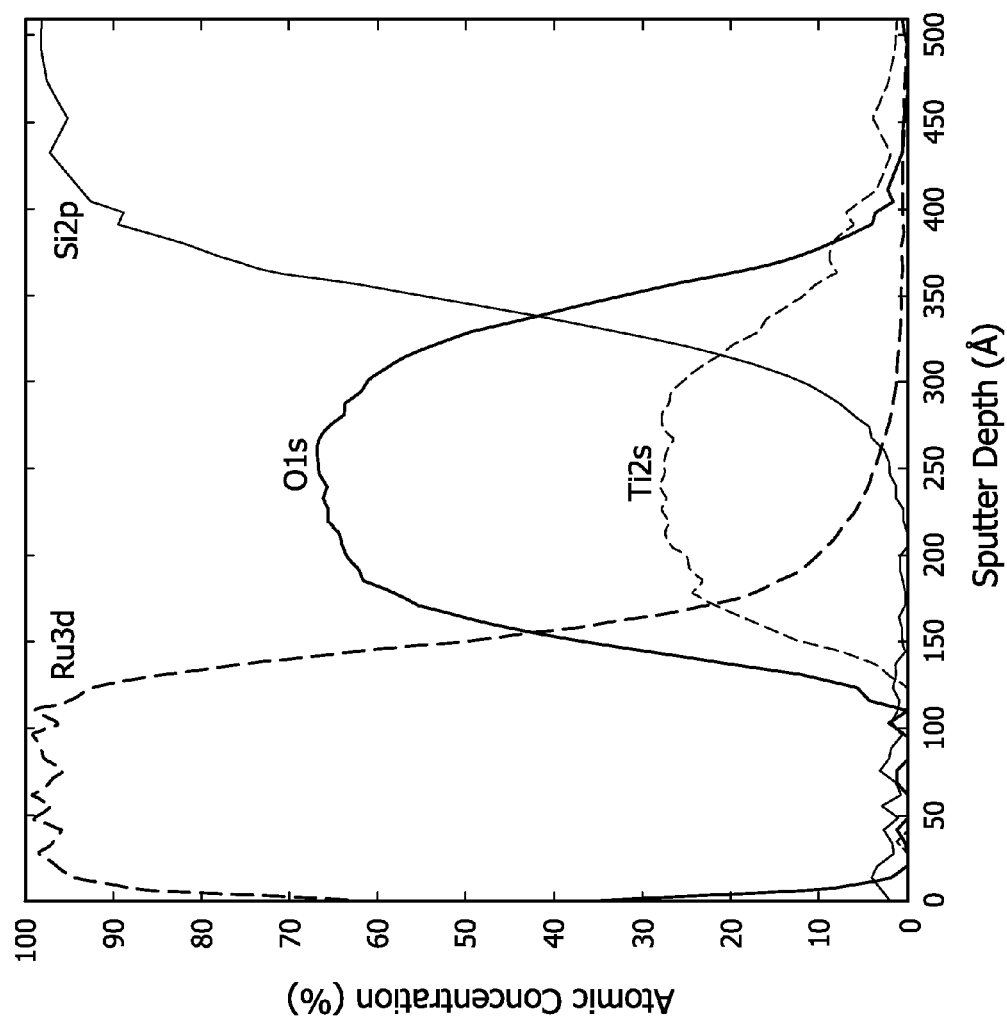
FIG. 6 is an X-ray Photo Electron Spectroscopy [XPS] of an ALD ruthenium film on $TiO_2$ using RuCp*DMDEP/oxygen at 300° C.

Example 6: Deposition of Ruthenium Metal Under ALD Conditions Using RuCp*DMDEP as Precursor and Oxygen as Reagent Ruthenium films were grown onto titanium oxide and titanium nitride coated silicon wafers under ALD conditions using a CN-1 showerhead style ALD reactor. The process cycle used was 50 sccm argon bubbled through RuCp*DMDEP at 138 C/600 sccm argon purge/100 sccm oxygen/600 sccm argon purge using cycle times of 5/20/5/20 seconds respectively. 600 sccm argon purge was comprised of 300 sccm purge of the precursor line and 300 sccm purge of the reagent line. Wafer temperature was 300 C, ALD chamber pressure was 3 Torr. Repeating this cycle 450 times yielded a ~15 nm Ru film whose XPS analysis is shown in FIG. 6. Secondary Ion Mass Spectrometry (SIMS) analysis of a ruthenium film grown under identical conditions for 300 process cycles showed carbon and oxygen levels of <1.0 atomic %.

A 9.3 nanometer (nm) ruthenium film was also grown onto a TiN substrate using identical process conditions as described herein in Example 6 (e.g., using RuCp*DMDEP/oxygen at 300° C.) and analyzed using Atomic Force Microscopy (AFM). The ruthenium film over an area 1.00 μm×1.00 μm×6.32 nm, was found to have a low surface roughness or a RMS of 0.31 nm as measured by AFM.

The invention claimed is:

1. A composition comprising one or more compounds having the following formulae 3A, 3B, and 3C:

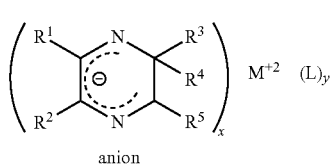
anion
Formula 3A

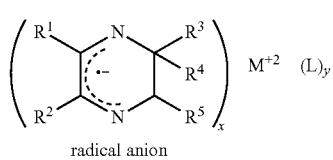
radical anion
Formula 3B

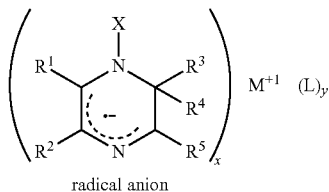
radical anion
Formula 3C wherein $R^1$, $R^2$, $R^3$, $R^4$ are each independently selected from a $C_1$-$C_6$ linear, branched or cyclic alkyl group; $R^5$ is independently selected from a H atom and a $C_1$-$C_6$ linear, branched, or cyclic alkyl group; (L) is an anion selected from cyclopentadienyl, pentaalkylcyclopentadienyl, pentamethylpentadienyl, dimethylpentadienyl, trimethylpentadienyl, methylcyclopentadienlyl, ethylcyclopentdienyl, imidazolyl, trialkylimidazolyl, pyrrolyl, and alkyl pyrrolyl; M is a divalent metal; x=1 or 2; x+y=2; X is independently selected from a H atom, a $C_1$-$C_6$ linear, branched, or cyclic alkyl group, and $SiR^6$ and where $R^6$ is independently selected from a $C_1$-$C_3$ linear or branched alkyl group.

2. A composition comprising one or more compounds having the following formulae 3F, 3G, and 3H:

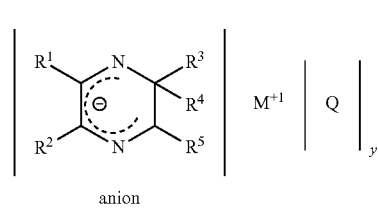
anion
Formula 3F

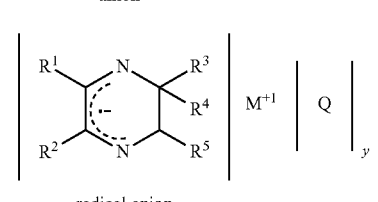
radical anion
Formula 3G

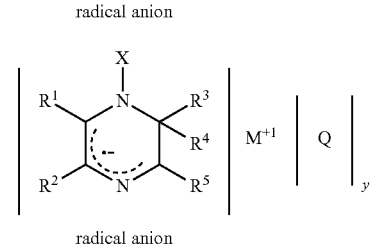
radical anion
Formula 3H wherein $R^1$, $R^2$, $R^3$, $R^4$ are each independently selected from a $C_1$-$C_6$ linear, branched or cyclic alkyl group; $R^5$ is independently selected from a H atom and a $C_1$-$C_6$ linear, branched, or cyclic alkyl group; (Q) is a neutral ligand selected from the group consisting of benzene, an alkylated benzene; M is a monovalent metal; y=1; X is independently selected from a H atom, a $C_1$-$C_6$ linear, branched, or cyclic alkyl group, and $SiR^6$ and where $R^6$ is independently selected from a $C_1$-$C_3$ linear or branched alkyl group.

* * * * *